(12) United States Patent
Stallinga et al.

(10) Patent No.: US 8,991,270 B2
(45) Date of Patent: Mar. 31, 2015

(54) METHOD AND APPARATUS FOR RAPID FILTER ANALYSIS OF FLUID SAMPLES

(75) Inventors: Sjoerd Stallinga, Eindhoven (NL); Stefano Cattaneo, Landquart (CH)

(73) Assignee: Koninklijke Philips N.V., Eindhoven (NL)

( * ) Notice: Subject to any disclaimer, the term of this patent is extended or adjusted under 35 U.S.C. 154(b) by 904 days.

(21) Appl. No.: 13/130,586

(22) PCT Filed: Nov. 20, 2009

(86) PCT No.: PCT/IB2009/055229
§ 371 (c)(1),
(2), (4) Date: May 23, 2011

(87) PCT Pub. No.: WO2010/058373
PCT Pub. Date: May 27, 2010

(65) Prior Publication Data
US 2011/0220818 A1 Sep. 15, 2011

(30) Foreign Application Priority Data
Nov. 24, 2008 (EP) ..................................... 08305832

(51) Int. Cl.
*G01N 15/06* (2006.01)
*G01N 1/22* (2006.01)

(52) U.S. Cl.
CPC .......... *G01N 15/0625* (2013.01); *G01N 1/2205* (2013.01)
USPC .................................................... 73/863.02

(58) Field of Classification Search
USPC ............ 73/1.02, 863.2, 863.25, 28.4, 863.02, 73/28.04
See application file for complete search history.

(56) References Cited

U.S. PATENT DOCUMENTS

| | | | |
|---|---|---|---|
| 5,091,652 A | | 2/1992 | Mathies |
| 5,480,804 A | | 1/1996 | Niwa |
| 5,627,042 A | | 5/1997 | Hirose |
| 5,663,057 A | * | 9/1997 | Drocourt et al. ............. 435/40.5 |
| 5,739,003 A | | 4/1998 | Brocklehurst |
| 5,817,956 A | * | 10/1998 | Novick ........................ 73/865.5 |
| 5,821,066 A | | 10/1998 | Pyle |
| 5,891,394 A | * | 4/1999 | Drocourt et al. ................ 422/50 |
| 5,898,114 A | * | 4/1999 | Basch et al. ................ 73/863.23 |
| 6,096,272 A | | 8/2000 | Clark |

(Continued)

FOREIGN PATENT DOCUMENTS

| | | |
|---|---|---|
| DE | EP1830173 | 9/2007 |
| FR | EP0713087 | 4/1999 |

(Continued)

*Primary Examiner* — Hezron E Williams
*Assistant Examiner* — Xin Zhong (57) ABSTRACT

An apparatus for analyzing a fluid of volume V includes a filter having a filter surface or area A, the filter being capable of allowing the fluid to flow through the filter surface. The fluid's volumetric flow density, averaged over the filter surface, is $j_{mean}$. The apparatus further includes a scanner for scanning the filter surface with a scan rate B. The area A is optimized based on the volume V, the scan rate B and the volumetric flow density $j_{mean}$ to minimize the sum of filtering time and scanning time. Instead of one filter, at least two filters may be used each having a different area A. The apparatus also includes a mechanism for selecting one of the filters and placing the selected filter in an operating position, where the scanner scans the filter surface face of the selected filter.

12 Claims, 5 Drawing Sheets

(56) References Cited

U.S. PATENT DOCUMENTS

| | | |
|---|---|---|
| 6,122,396 A | 9/2000 | King |
| 6,711,283 B1 | 3/2004 | Soenksen |
| 6,779,411 B1 * | 8/2004 | Spurgeon .................. 73/863.23 |
| 6,803,208 B2 | 10/2004 | Seaver |
| 7,211,225 B2 | 5/2007 | Ferguson |
| 7,312,073 B2 | 12/2007 | Shaw |
| 7,867,779 B2 | 1/2011 | McDermott |
| 8,299,449 B2 | 10/2012 | Febo |
| 2003/0008341 A1 * | 1/2003 | Spurrell .......................... 435/34 |
| 2004/0038425 A1 * | 2/2004 | Ferguson et al. ............. 436/177 |
| 2004/0101210 A1 * | 5/2004 | Weinstein et al. ............ 382/284 |
| 2004/0243318 A1 | 12/2004 | Oqawa |
| 2005/0221403 A1 | 10/2005 | Gazenko |
| 2006/0172428 A1 * | 8/2006 | McDermott et al. ............ 436/63 |
| 2007/0207518 A1 | 9/2007 | Motoyama |
| 2008/0003610 A1 | 1/2008 | Frank |
| 2009/0225410 A1 | 9/2009 | Fey |
| 2010/0163761 A1 * | 7/2010 | Febo ............................. 250/573 |

FOREIGN PATENT DOCUMENTS

| | | |
|---|---|---|
| JP | 3009483 A | 1/1991 |
| JP | 2000210099 A | 8/2000 |
| RU | 2043618 C1 | 9/1995 |
| WO | WO9945094 | 9/1999 |
| WO | WO02075370 | 9/2002 |
| WO | WO03081212 | 10/2003 |
| WO | WO2008023325 | 2/2008 |

* cited by examiner

METHOD AND APPARATUS FOR RAPID FILTER ANALYSIS OF FLUID SAMPLES

FIELD OF THE INVENTION

In a first aspect the invention relates to an apparatus for analyzing a fluid of volume V, comprising
a filter having a filter surface of area A, the filter being capable of allowing the fluid to flow through the filter surface, the fluid's volumetric flow density, averaged over the filter surface, being $j_{mean}$; and
a scanner for scanning the filter surface with a scan rate B.

In a second aspect the invention relates to a method of analyzing a fluid of volume V, the method comprising the subsequent steps of
making the fluid flow through a filter surface of a filter, the fluid's volumetric flow density, averaged over the filter surface, being $j_{mean}$; and
scanning the filter surface with a scan rate B.

In a third aspect the invention relates to an apparatus for analyzing a fluid, the apparatus comprising
a filter having a filter surface of area A, the filter being capable of allowing the fluid to flow through the filter surface; and
a scanner for scanning the filter surface.

In a fourth aspect the invention relates to an apparatus for analyzing a fluid.

BACKGROUND OF THE INVENTION

Microbiological analysis of fluid samples has important biological, medical, and industrial applications, for example, in clinics, in the food and beverage, pharmaceutical, personal care products, and environmental sectors. In general such analysis is aimed at determining the presence or absence of microorganisms in the sample, quantifying the amount of microorganisms present, and in some cases identifying an unknown microorganism to various levels of detail. Current standard methods of testing are often based on cell culturing, and take time to results of days to weeks depending on the type of sample and microorganism. There is a great need for microbiological analysis with increased throughput.

An example of such a rapid method is the one proposed by AES Chemunex (http://www.aeschemunex.com/). Their FDA-approved ScanRDI-system performs the analysis by laser scanning cytometry of filtered products. The steps of this method are filtering the fluid sample, staining the possibly present microbiological contaminants with a fluorescent dye, optically scanning the surface of the filter with a large laser spot (5-10 µm) for detecting the possibly present microbiological contaminants, and imaging the areas surrounding the contaminants with a high-resolution (0.5 µm) microscope having an automated stage. Aspects of the technique have been described in EP 0 713 087 B1.

An improved filter technology is provided by fluXXion (http://www.fluxxion.com/). The technique is based on lithographically defined micro-sieves, which have a single well-defined pore size (down to 0.2 µm), are optically flat (which is advantageous from the point of view of the subsequent optical scanning steps and also results in reduced backscattering) and thin so as to offer a low flow resistance and hence a higher filtration throughput compared to conventional membrane filters made from porous materials such as cellulose, nylon, polyvinyl chloride, polysulfone, polycarbonate, and polyester.

Existing devices and methods generally employ filters with pre-defined dimensions and only optimize the parameters of the filtering process, such as the flow-through speed, and of the scanning process, such as scanning speed and beam diameter. For example, the ScanRDI-system of AES Chemunex uses standard 25 mm membrane filters, usually polyester ChemFilters CB04 with a pore size of 0.45 µm.

It is an object of the invention to provide a particularly fast method and a particularly fast apparatus for filtering a given amount of a fluid and subsequently scanning the filter. In particular, it is an object of the invention to provide a method and apparatus that is faster than the prior art described above.

This object is achieved by the features of the independent claims. Further specifications and preferred embodiments are outlined in the dependent claims.

SUMMARY OF THE INVENTION

According to a first aspect of the invention, the area A of the filter surface substantially coincides with an optimum area $A_{opt}$ defined as $$A_{opt} = \sqrt{\frac{VB}{j_{mean}}}.$$

This allows reducing the total assay time considerably, as will be explained below. Preferably A differs from $A_{opt}$ at most by 20%. More preferably A differs from $A_{opt}$ at most by 10%. Even more preferably A differs from $A_{opt}$ at most by 5%. Analyzing the fluid may in particular comprise detecting the presence of small material objects, in particular biological objects such as bacteria or fungi. However, in principal the invention is applicable to all applications in which a given volume of a fluid is filtered at a constant (time-independent) flow rate and a filter surface is subsequently scanned at a constant (time-independent) scan rate.

The apparatus may further comprise a container for holding the fluid, the container having an outlet for being connected to the filter, wherein the container's capacitance coincides with the volume V. This facilitates choosing the volume of the fluid such that the total assay time will be minimal, or nearly minimal, for the chosen volume.

The apparatus may further comprise driving means for making the fluid flow through the filter. The driving means may, for example, comprise a pump situated either upstream or downstream of the filter. Providing the pump downstream of the filter may be advantageous in that the pump will be less affected by impurities contained in the fluid if these are filtered out by the filter. The driving means may alternatively be provided by placing a container containing the fluid on a higher level than the filter. Thus the fluid's potential energy in the gravitational field of the Earth can be used to drive the fluid through the filter.

The volumetric flow density $j_{mean}$ of the fluid and the scan rate B may in particular be a maximum volumetric flow density and a maximum scan rate, respectively, that can be attained by the apparatus. The allowable volumetric flow density $j_{mean}$ is usually limited by the properties of the fluid and the filter. Increasing the pumping pressure over a certain threshold would result in damage to the filter. Similarly, the scanner has a certain maximum scan rate which cannot easily be increased. Of course it is conceivable to operate the apparatus at a flow density less than $j_{mean}$ and/or at a scan rate less than B, but in practice the device will be operated at its maximum flow rate and its maximum scan rate. For such a system it is particularly advantageous to adapt the area of the filter surface to the maximum flow density and the maximum scan rate.

The scanner may comprise at least one of the following:
an automated microscope for mechanically scanning the filter area in steps, taking images at each step and then stitching the images in software to form an overall image;
a mechanism for scanning the filter surface in a continuous manner, and stroboscopic illumination means;
a mechanism for scanning the filter surface in a continuous manner, and a line camera or a Time Delay Integration camera;
an array of micro-objective lenses for scanning the whole filter area in a single continuous scan;
means for scanning a focused laser across the filter area;
means for scanning an array of focused laser spots across the filter area. These aspects will be discussed in greater detail further below.

The filter may comprise elementary filters arranged in parallel with regard to the flow of the fluid, each of the elementary filters having an elementary filter surface, the area A of the filter surface being the total area of the elementary filter surfaces.

The scanner may comprise elementary scanners for scanning the filter surface simultaneously, each scanner having an elementary scan rate, the scan rate B being the sum of the elementary scan rates. The elementary scanners may move independently, or they may be coupled. For example, a single motor could be used to displace an entire array of elementary laser beams relative to the filter surface.

The apparatus may further comprise a mechanism for adjusting the area A of the filter surface. Thus the total assay time may be minimized as a function of the fluid volume V, the scan rate B, and the averaged volumetric current density $j_{mean}$.

The apparatus may further comprise a controller for controlling the mechanism as a function of the volume V, the scan rate B, and the mean volumetric flow density $j_{mean}$.

Analogously, in the method according to the second aspect of the invention, the area A substantially coincides with an optimum area $A_{opt}$ defined as $$A_{opt} = \sqrt{\frac{VB}{j_{mean}}}.$$

The method may further comprise a step of adjusting the filter surface so as to adapt the area A to the volume V, the scan rate B, and the mean volumetric flow density $j_{mean}$. Here and throughout the filter surface is understood to be that part of the filter surface that is effectively used to filter the fluid. Hence its area A can be varied by bringing only a part of the filter's physical surface into contact with the fluid, e.g. by sealing a portion of the filter's physical surface, or by connecting the physical surface to an aperture having the desired size.

The apparatus according to the third aspect of the invention comprises a mechanism for adjusting the filter surface so as to vary the area A.

The apparatus may further comprise a controller for controlling the mechanism to vary the area A so as to minimize the sum of a filtering time and a scanning time, the filtering time and the scanning time being, respectively, a time required for filtering the fluid and a time required for scanning the filter surface.

According to the fourth aspect of the invention, an apparatus for analyzing a fluid comprises a set of at least two filters, each filter in the set of filters having a filter surface of area A and being capable of allowing the fluid to flow through the filter surface, the area A having a different value for each of the filters; and
a mechanism for selecting one of the filters and placing the selected filter in an operating position;
a scanner for scanning the filter surface of the selected filter.

The apparatus may further comprise a controller for controlling the mechanism to select the filter so as to minimize the sum of a filtering time and a scanning time, the filtering time and the scanning time being, respectively, a time required for filtering the fluid and a time required for scanning the filter surface. The controller may comprise an electronic control unit.

The presence of microorganisms in fluid samples is typically detected by a three-step process of filtration, staining, and optical detection. A prominent feature of the proposed method is the fact that the area of the filter is optimized on the basis of the sample volume and properties of both filter and scanner, in order to minimize the total assay time. As shown below, a minimum assay time can be achieved when the filtering and scanning steps take approximately the same time.

The invention is based on the insight that the different steps of the process each require a time that depends on the cross-sectional area A of the filter in a certain manner. Suppose the filter has an "open" fraction η (area of the pores divided by the total area) and supports the filtration of a volume V with a flow-through velocity u. The filtration then takes a time $$T_{filt} = \frac{V}{\eta u A}.$$

The flow-through velocity u in the pores is related to an averaged volumetric current density j (i.e. the volume flow through a unit area per unit time) by j=ηu, where j has been averaged over a region that is large compared to the pores of the filter, assuming that the flow-through velocity u is the same in all pores over which the average has been taken. The volumetric current density averaged over the entire cross section of the filter is denoted $j_{mean}$.

The flow-through velocity is limited not only by the characteristics of the filter used but also by the need to maintain the viability of the cells. It may be assumed that the time needed for the staining step is independent of the cross-sectional area of the filter.

Finally, suppose that the optical scanner can scan an area per unit time B. The scanning process then takes a time:

$$T_{scan} = \frac{A}{B}.$$

The total time (apart from the constant time needed for the staining and other possible steps) is thus given by:

$$T = T_{filt} + T_{scan} = \frac{V}{\eta u A} + \frac{A}{B}.$$

Clearly, this equation shows that there is a trade-off between filtration and scanning time. A small filter area gives rise to slow filtration and fast scanning, whereas a large filter area gives rise to fast filtration and slow scanning. It turns out that this trade-off has a distinct optimum. The total time is minimum for an area $$A_{opt} = \sqrt{\frac{VB}{\eta u}}.$$

In this optimum, the time needed for filtration and the time needed for scanning are equal and given by:

$$T_{filt} = T_{scan} = \sqrt{\frac{V}{\eta u B}}.$$

Consider for example a typical case in which a volume V=100 ml is filtered by a circular filter with radius 25 mm, open fraction 25% and flow-through velocity of 1 mm/sec. The time needed for filtration is about 3.4 minutes. A typical line scanner with 4096 pixels and 3 kHz line rate scans 0.768 mm²/sec at a resolution of 0.25 µm/pixel, thus taking 42.6 minutes for scanning the whole filter area. According to the above argument, the optimum filter area is 554 mm², which corresponds to a circle with radius 13.3 mm. The total time for filtration and scanning is now 12.0 minutes, with an overall improvement of assay time (excluding staining time) of 46 minutes to 24 minutes, nearly a factor of two.

A method for rapid microbiological analysis of fluid samples may comprise the steps of filtering the fluid sample with a micro-sieve, staining the possibly present microbiological contaminants on the surface of the micro-sieve with a (fluorescent) dye, and optically scanning the surface of the micro-sieve for detecting and imaging the possibly present microbiological contaminants, characterised by the time taken by the filtering step being substantially equal to the time taken by the scanning step.

An apparatus for carrying out this method may comprise a container for holding a fluid sample of volume V, a filter for filtering the fluid sample with cross-sectional area A, a fraction of the filter area occupied by pores η, and a flow-through velocity u, and an optical scanner for scanning the area of the filter that scans an area per unit time B, the filter cross-section area being chosen substantially equal to √(VB/ηu).

Various scanner techniques may be used. A first type of scanner is an automated microscope which mechanically scans the filter area in steps, takes images with a rectangular camera (number of pixels in both x and y larger than 1) at each step and then stitches the images in software to form an overall image. A second type uses a continuous mechanical scan and stroboscopic illumination to prevent motion blur. A third type of scanner uses a continuous mechanical scan and a line camera (number of pixels in either x or y equal to 1). A fourth type of scanner uses a TDI (Time Delay Integration) camera, which is a rectangular camera that uses the plurality of lines for a plurality of exposures of the sample. The output of the camera is thus the same as for a line camera. However this type of camera makes more efficient use of the illumination light. A fifth type of scanner uses an array of micro-objective lenses allowing for scanning the whole filter area in a single continuous scan. A sixth type of scanner makes use of scanning a focused laser spot across the filter area. A seventh type of scanner uses an array of focused laser spots, which is advantageous from the point of view of scanning speed. Lasers allow for a power in the focal area that is much higher than the saturation intensity for typical fluorophores. Illuminating fluorophores in the saturation regime can be disadvantageous from the point of view of signal linearity and relative occurrence of photobleaching. It can therefore be advantageous to divide the total available laser power over a multitude of spots, each spot reaching an intensity below the fluorescence saturation level.

The key idea of the invention can be generalized to an embodiment using multiplexing and batch processing. Suppose that N samples are filtered simultaneously by N micro-sieves, then stained simultaneously as well, and finally scanned by an apparatus comprising M scan elements with throughput B per scan element. The time needed for the filtration and staining steps are unchanged, but the time needed for the scanning step is now:

$$T_{scan} = \frac{NA}{MB}.$$

The total time per sample (apart from the constant time needed for the staining and possible other steps) is thus given by:

$$T = \frac{T_{filt} + T_{scan}}{N} = \frac{V}{N\eta uA} + \frac{A}{MB}.$$

This total time is optimum (minimum) for an area:

$$A_{opt} = \sqrt{\frac{VMB}{N\eta u}}.$$

In this optimum the time needed for filtration and the time needed for scanning are equal and given by:

$$T_{filt} = T_{scan} = \sqrt{\frac{NV}{\eta u MB}}.$$

The total time per sample is now:

$$T = 2\sqrt{\frac{V}{\eta u NMB}}.$$

A first advantage of this embodiment is the gain with a factor $1/\sqrt{NM}$ in total time per sample. A second advantage can be in terms of cost. This embodiment describes for example the case of batch processing (N>1, M=1) with a relatively rapid scanner (B large). The optimum area of the filter will be relatively large if the samples are processed consecutively with such a fast scanner. As the cost of the disposable filter is likely to increase with size (and hence filter area), there is also a cost reduction by the use of batch processing, namely with a factor $1/\sqrt{N}$ per disposable micro-sieve (assuming that the cost is proportional to the filter area). Similarly, if a large filter area is scanned by a relatively slow and inexpensive scanner then multiplexing (N=1, M>1) results in gains.

For example, a fast Time Delay and Integration (TDI) line scanner with 4096 pixels and a 50 kHz line rate allows for a throughput of 12.8 mm²/sec at a resolution of 0.25 µm/pixel.

Processing N=4 samples simultaneously and scanning the N=4 samples sequentially with this scanner gives an optimum filter area of 1131 mm², which corresponds to a circle with radius 19.0 mm (assuming the same sample volume, open fraction and flow-through velocity as in the previous sample). The total scanning and filtration time are equal to 5.9 min, so an assay time of 3.0 min per sample.

Many applications will make use of a fixed scanner, filter type, and sample volume. In that case, the optimum filter size will have to be defined only once and the same size could be used in all subsequent assays. In case of applications requiring variable sample volumes and/or filter characteristics (e.g. sieve size, porosity, etc. . . . ), the apparatus could include means for changing the portion of the filter used in the assay, for example fluidic adapters with apertures of variable sizes, or a single aperture with adjustable size.

In summary, means and methods for rapid microbiological analysis of fluid samples are proposed. The methods typically comprise steps of filtering the fluid sample with a micro-sieve, staining the possibly present microbiological contaminants on the surface of the micro-sieve with a dye, for example a fluorescent dye, and optically scanning the surface of the micro-sieve for detecting and imaging the possibly present microbiological contaminants or other particles or objects caught by the sieve. The area of the micro-sieve can be optimized on the basis of the sample volume (or the amount of substance) and the properties of both filter and scanner in order to minimize the total assay time. In particular, it is shown that a minimum assay time is achieved when the filtering and scanning steps take approximately the same time.

An apparatus for carrying out this method is also proposed. According to an exemplary embodiment, the apparatus comprises a container for holding a fluid sample of volume V, a filter for filtering the fluid sample with cross-sectional area A, a fraction of the filter area occupied by pores, and a flow-through velocity u, and an optical scanner for scanning the area of the filter that scans an area per unit time B. Preferably the filter's cross-sectional area is substantially equal to the optimum value $\sqrt{(VB/\eta u)}$, in the sense that it differs from the optimum value by at most, say, 5% or 10% or 20% or 30%. The concept also holds for a case in which N samples are filtered simultaneously by N micro-sieves, then stained simultaneously as well, and finally scanned by an apparatus comprising M scan elements.

DESCRIPTION OF PREFERRED EMBODIMENTS

Unless specified otherwise, identical or similar reference numerals appearing in different Figures label identical or similar components.

Figure 1:
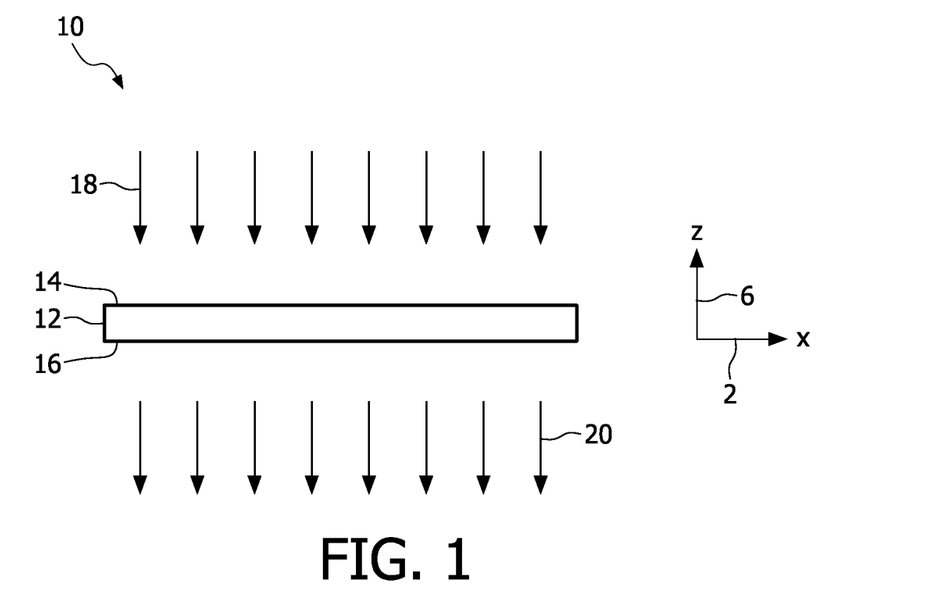
FIG. 1 schematically illustrates a filter and a fluid flowing through the filter.

FIG. 1 provides a schematic side view of apparatus 10 having a filter 12 and a fluid 18 flowing through the filter 12. The fluid may in particular be an aqueous solution. The fluid is typically in a liquid phase, but it could also be in the gas phase. The filter 12 has an entrance surface 14 and an exit surface 16. The entrance surface 14 and the exit surface 16 form parallel planes extending perpendicular to the plane of the Figure. The fluid 18 enters the filter 12 through the entrance surface 14 and leaves the filter 12 through the exit surface 16. The fluid leaving the filter is labelled 20. The filter 12 may, for example, be a membrane filter or a micro-sieve. The filter 12 and the fluid 18, 20 are surrounded by a tube (not shown) running in the z-direction 6. While the fluid 18 flows through the filter 12, microscopic objects, such as single cells or other microorganisms, are stopped by the filter and accumulate on or near its entrance surface 14. The entrance surface 14 has total area A. The fluid's volumetric flow rate is the volume of the amount of fluid that passes through the filter in a given time interval, divided by the length of the time interval. The volumetric flow rate is substantially constant during the filtering process. The volumetric flow rate divided by the area A is referred to as the mean volumetric flow density $j_{mean}$. In contrast, the fluid's local volumetric flow density j is defined at any point within the fluid 18, 20. The local flow density j may be somewhat lower toward the margins of the filter as compared to the central flow region, but generally the local flow density j and the mean flow density $j_{mean}$ are substantially the same across the entrance surface 14. The total time for filtering the fluid 18 is $$T_{filt} = \frac{V}{j_{mean} A},$$

V being the volume of the fluid 18, 20. The filter offers a certain resistance to the fluid as the latter is forced through the filter. To a certain extent, the resistance increases as the force by which the fluid is forced through the filter increases, resulting in a mean flow density $j_{mean}$ that is substantially independent of that force, at least within a certain parameter range. Therefore the flow density $j_{mean}$ may be considered an intrinsic property of the filter 12 and the fluid 18. Of course, the volumetric flow density $j_{mean}$ may have a different value for fluids other than aqueous solutions, e.g. oils.

Figure 2:
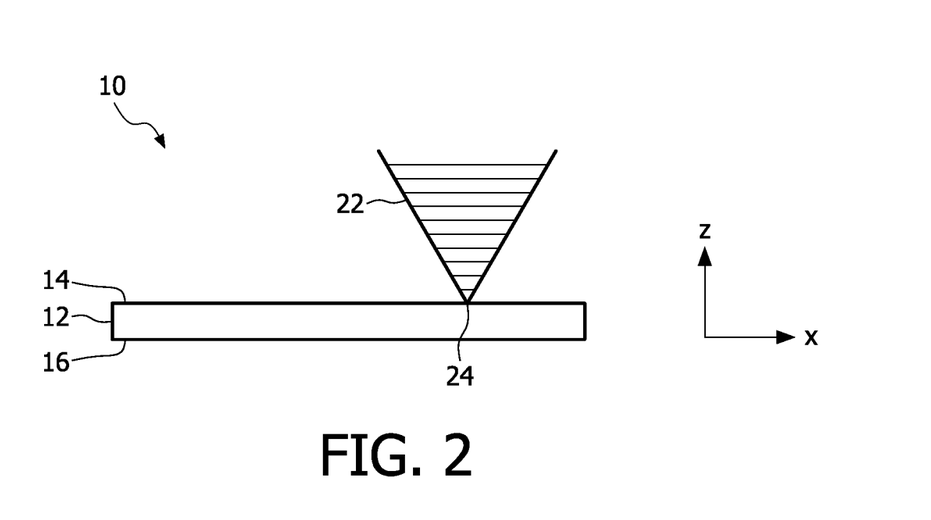
FIG. 2 schematically illustrates the filter and a laser beam focused on a filter surface from an entrance side of the filter.

After the fluid 18 has flown through the filter 12, a filter surface (in the present example, the entrance surface 14) of the filter 12 may be scanned by a scan head 22, as shown schematically in FIG. 2. The scan head 22 illuminates and images a fraction of the entrance surface 14 and the imaged fraction is moved relative to the surface 14 with a scan rate B, the scan rate being the scanned area per time. The scan rate B is determined by the properties of the scanning mechanism, for example, by the framerate and number of pixels of the image sensor (not shown), or by the level of illumination, or by the speed of a motor (not shown) for displacing optical elements (not shown) so as to move the laser beam 22 across the surface 14. Light reflected by objects at the focal point 24 or fluorescent light emitted by objects at the focal point 24 is detected by a detector (not shown) and analyzed so as to detect these objects on the surface 14. The total time for scanning the entrance surface 14 is $$T_{scan} = \frac{A}{B}.$$

The area A has been chosen equal to $$\sqrt{\frac{VB}{j_{mean}}},$$

so as to minimize the total time, $T_{filt}+T_{scan}$. It is also possible to scan the entrance surface 14 by more than one scan head. The scan rate B then refers to the combined scan rate, i.e. the sum of the scan rates of the individual scan heads.

It is noted that the filter 12 can be illuminated from either side, that is, from its entrance side as well as from its exit side. Furthermore the filter 12 can imaged from either side, giving a total of four possible combinations for illumination and imaging. However, preferably both illumination and imaging are on the entrance side (here, the top side) of the filter 12.

Figure 3:
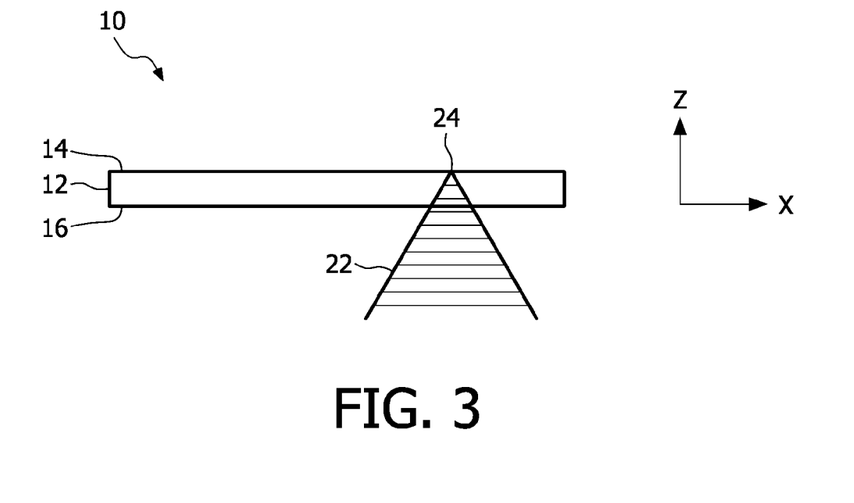
FIG. 3 schematically illustrates the filter and a laser beam focused on the filter surface from an exit side of the filter.

FIG. 3 illustrates an embodiment in which the scan head 22 is arranged on the exit side of the filter 12. In the example shown, detection light emitted by the scan head 22 traverses the filter 12, which supposes that the filter 12 is sufficiently thin or transparent.

Figure 4:
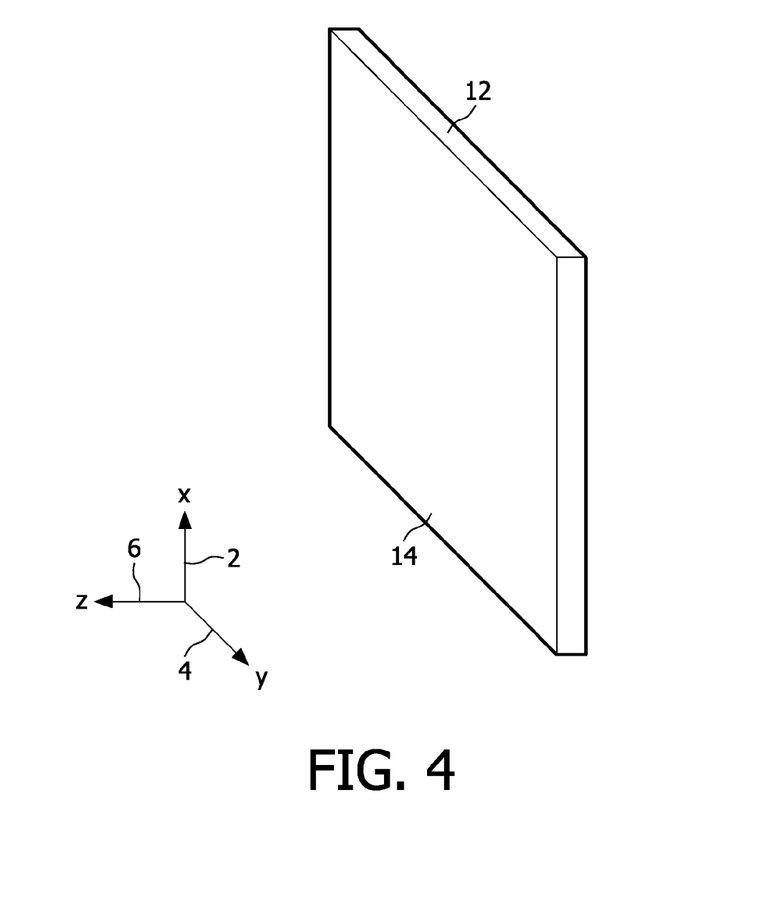
FIG. 4 provides a schematic skew-angle view of the filter.

FIG. 4 provides a simplified three-dimensional view of the filter 12 showing x,y,z directions 2, 4, 6, respectively. In the embodiment shown, the entrance surface 14 is rectangular, but it may have different shapes. The entrance surface 14 may in particular be circular, as this may produce a particular uniform flow of the fluid through the filter 12.

Figure 5:
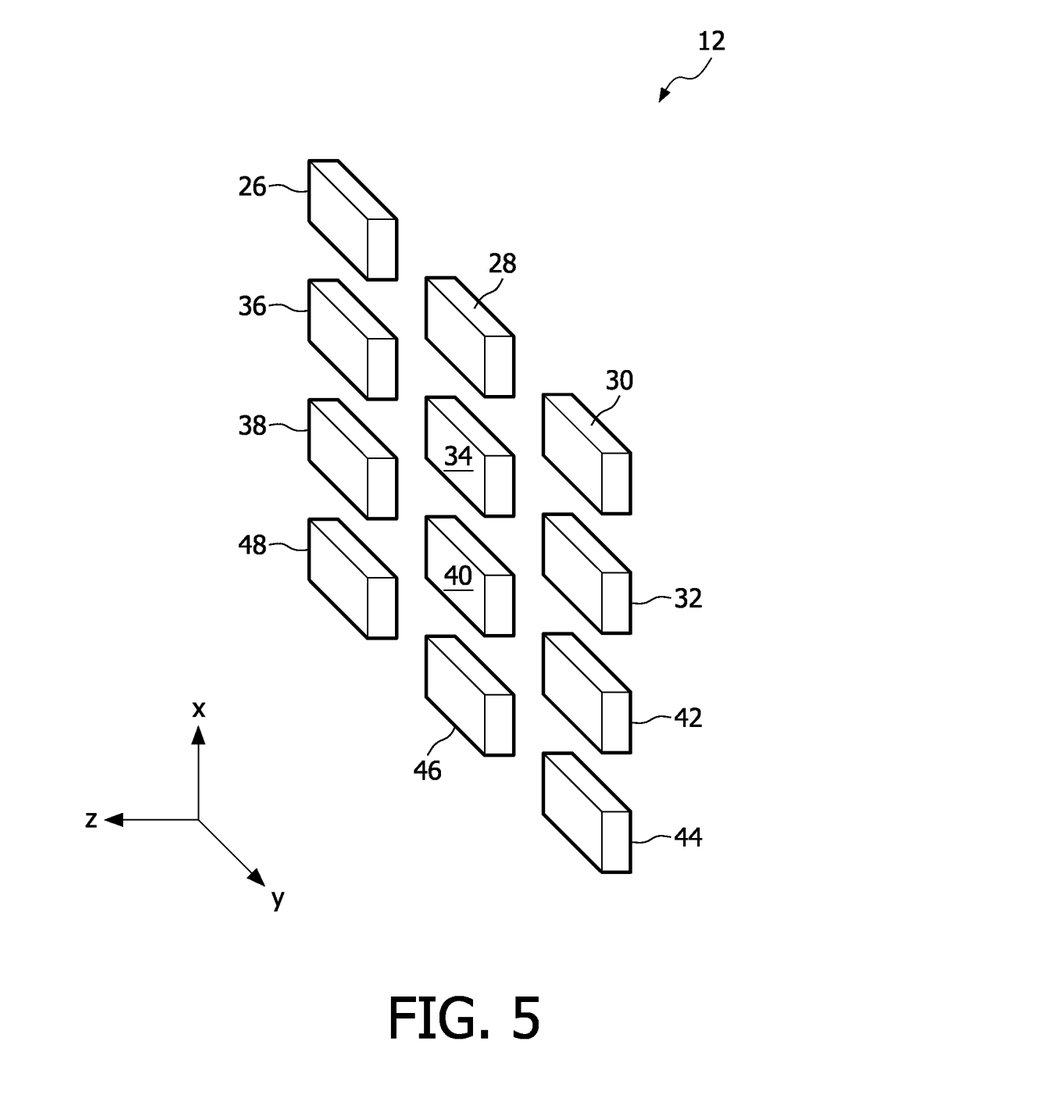
FIG. 5 provides a schematic skew-angle view of a filter comprising an array of elementary sieves.

FIG. 5 illustrates an alternative embodiment in which the filter 12 is composed of elementary filters or sieves 26, 28, 30, 32, 34, 36, 38, 40, 42, 44, 46, 48 having a combined filter surface of area A.

Figure 6:
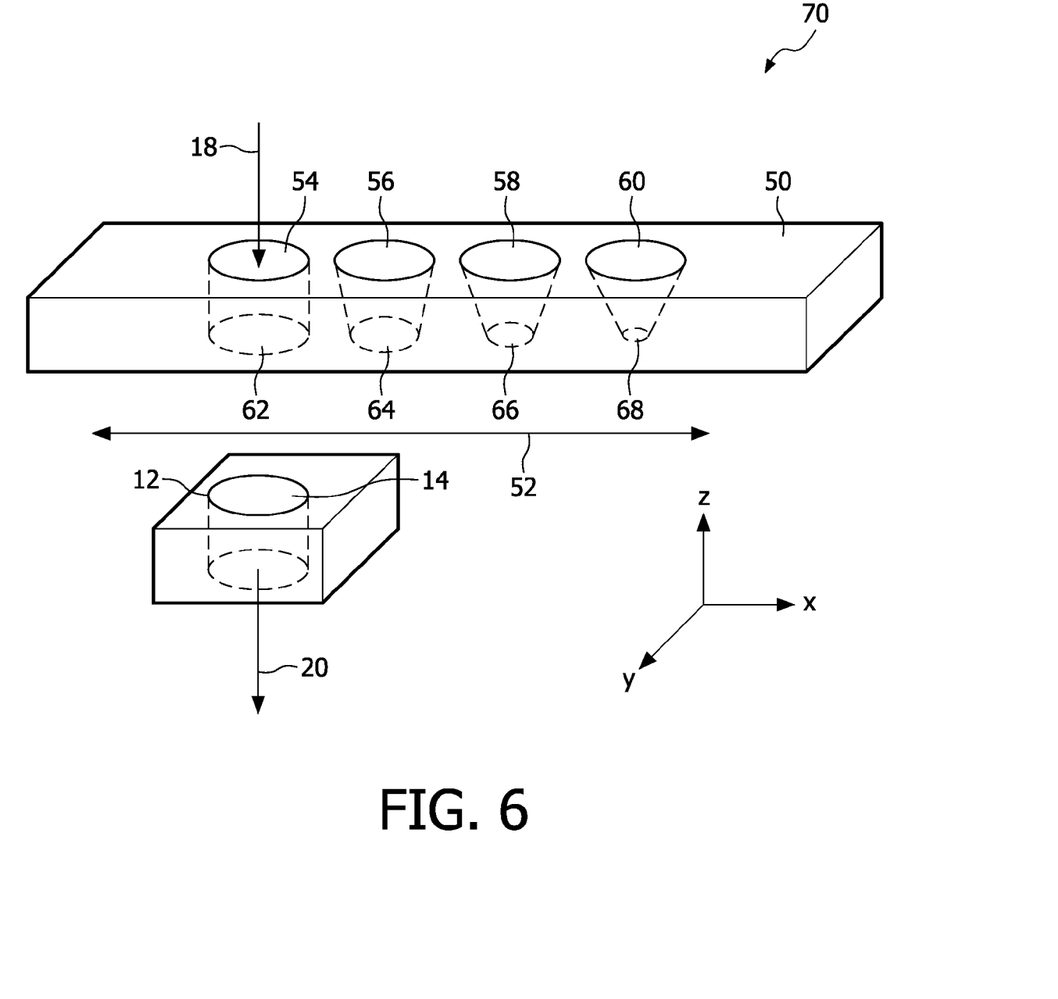
FIG. 6 schematically illustrates a mechanism for adapting the cross-sectional area of a filter.

Referring now to FIG. 6, there is shown a system comprising a filter 12 for filtering a fluid 18 and an adapter 70 for adapting the effective size of the entrance surface 14. The adapter 70 comprises a slide 50 having four apertures 54, 56, 58, 60 traversing the slide 50 in a vertical direction (z direction) parallel to the flow direction. The apertures 54, 56, 58, 60 have exit cross sections 62, 64, 66, 68 which differ in their area A. In the configuration shown, the aperture 54 is situated above the filter 12. By displacing the slide 50 in a horizontal direction (x direction), as indicated by the arrow 52, one of the other apertures 56, 58, 60 can instead be placed above the filter 12 so as to vary the effective area A of the entrance surface 14 of the filter 12. Thus the entrance surface 14 may be adapted, for example, as a function of the volume V of the fluid 18 that is to be filtered. The apertures 54, 56, 58, 60 communicate with containers (not shown) for holding the fluid, the capacity of each container being given by $$V = \frac{A^2 j_{mean}}{B}$$

where A is the area of the exit cross section (62, 64, 66, or 68) of the respective aperture (54, 56, 58, or 60), B is the scan rate of the scanning device (not shown) for scanning the entrance surface 14, and $j_{mean}$ is the volumetric flow density of the fluid 18 averaged over the entrance surface 14. In a related embodiment (not shown), the apertures 54, 56, 58, 60 are arranged along a circle.

Figure 7:
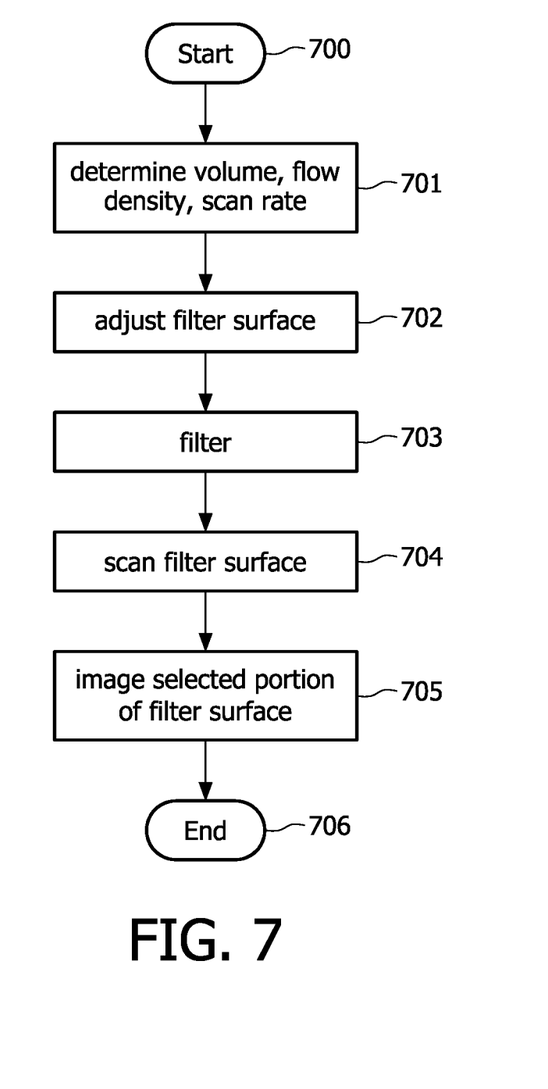
FIG. 7 is a flow-chart illustrating steps of analyzing a fluid.

Referring now to FIG. 7, there is represented a flow chart of a method of analyzing a fluid sample, wherein the fluid 18 is to be passed through a filter. In a first step 701, the volume V of the fluid to be sampled, the expected volumetric flow density $j_{mean}$, and the scan rate B of a scanner for scanning a filter surface are determined. The filter surface is then adapted such that its effective area A is as nearly equal to $$\sqrt{\frac{VB}{j_{mean}}}$$

as possible (step 702). The filter surface may be any surface of or in the filter that is traversed by all of the fluid. The filter surface may in particular be an entrance surface of the filter. In a subsequent step 703 the fluid is passed through the filter. The filter surface A is then scanned by means of the scanner with scanning rate B (step 704) to locate possibly present objects on the filter surface. Finally, a selected region of the filter surface in which the presence of an object of interest has been detected is imaged via a microscope (step 705).

While the invention has been illustrated and described in detail in the drawings and in the foregoing description, the drawings and the description are to be considered exemplary and not restrictive. The invention is not limited to the disclosed embodiments. Equivalents, combinations, and modifications not described above may also be realized without departing from the scope of the invention.

The verb "to comprise" and its derivatives do not exclude the presence of other steps or elements in the matter the "comprise" refers to. The indefinite article "a" or "an" does not exclude a plurality of the subjects the article refers to. It is also noted that a single unit may provide the functions of several means mentioned in the claims. The mere fact that certain features are recited in mutually different dependent claims does not indicate that a combination of these features cannot be used to advantage. Any reference signs in the claims should not be construed as limiting the scope.

The invention claimed is:

1. An apparatus for analyzing a fluid of volume V, comprising:
a filter having a filter surface of area A, the filter being configured to allow the fluid to flow through the filter surface at a volumetric flow rate, the volumetric flow rate divided by the area A being a mean volumetric flow density $j_{mean}$; and
a scanner for scanning the filter surface with a scan rate B;
wherein the area A is substantially equal to an optimum area Aopt defined as $$A_{opt} = \sqrt{\frac{VB}{j_{mean}}}.$$

2. The apparatus according to claim 1, further comprising a pump configured to drive the fluid flow through the filter.

3. The apparatus as set forth in claim 2, wherein the volumetric flow density $j_{mean}$ of the fluid is a maximum volumetric flow density attainable by the apparatus and the scan rate B is a maximum scan rate attainable by the apparatus.

4. The apparatus according to claim 1, further comprising a mechanism for adjusting the area A of the filter surface.

5. The apparatus as set forth in claim 4, further comprising a controller for controlling the mechanism as a function of the volume V, the scan rate B, and the mean volumetric flow density $j_{mean}$.

6. The apparatus as set forth in claim 1, further comprising a container for holding the fluid, the container having an outlet for being connected to the filter, wherein the container's capacitance coincides with the volume V.

7. The apparatus according to claim 1, wherein the scanner comprises at least one of the following:
- an automated microscope for mechanically scanning the filter area in steps, taking images at each step and then stitching the images in software to form an overall image;
- a mechanism for scanning the filter surface in a continuous manner, and stroboscopic illumination means;
- a mechanism for scanning the filter surface in a continuous manner, and a line camera or a Time Delay Integration camera;
- an array of micro-objective lenses for scanning the whole filter area in a single continuous scan;
- means for scanning a focused laser across the filter area; and
- means for scanning an array of focused laser spots across the filter area.

8. The apparatus according to claim 1, wherein the filter comprises elementary filters arranged in parallel with regard to the flow of the fluid, each of the elementary filters having an elementary filter surface, the area A of the filter surface being a total area of the elementary filter surfaces.

9. The apparatus according to claim 1, wherein the scanner comprises elementary scanners for scanning the filter surface simultaneously, each scanner having an elementary scan rate, the scan rate B being a sum of the elementary scan rates.

10. The apparatus of claim 1, wherein the mean volumetric flow density $j_{mean}$ is substantially independent of a force used to force the fluid through the filter.

11. A method of analyzing a fluid of volume V, comprising the acts of:
- making the fluid flow through a filter surface of a filter, the fluid's volumetric flow density, divided by an area of the filter surface, being $j_{mean}$, and
- scanning the filter surface with a scan rate B;
- wherein the area of the filter surface is substantially equal to an optimum area $A_{opt}$ defined as $$A_{opt} = \sqrt{\frac{VB}{j_{mean}}}.$$

12. The method as set forth in claim 11, further comprising an act of adjusting the filter surface so as to adapt the area A to the volume V, the scan rate B, and the mean volumetric flow density $j_{mean}$.

* * * * *